(12) United States Patent
Nutalapati et al.

(10) Patent No.: US 10,064,820 B2
(45) Date of Patent: *Sep. 4, 2018

(54) ANTIHISTAMINE COMPOSITIONS, COMBINATIONS, AND USE THEREOF

(71) Applicant: APTAPHARMA INC., Pennsauken, NJ (US)

(72) Inventors: Siva Rama K. Nutalapati, Princeton, NJ (US); Prahlad Patel, Voorhees, NJ (US); Nisha Sureshbhai Patel, Maple Shade, NJ (US)

(73) Assignee: APTAPHARMA INC., Pennsauken, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/281,144

(22) Filed: Sep. 30, 2016

(65) Prior Publication Data

US 2018/0092837 A1    Apr. 5, 2018

(51) Int. Cl.
| | |
|---|---|
| *A61K 9/20* | (2006.01) |
| *A61K 31/501* | (2006.01) |
| *A61K 9/00* | (2006.01) |
| *A61K 31/445* | (2006.01) |
| *A61K 31/135* | (2006.01) |
| *A61K 31/47* | (2006.01) |
| *A61K 31/404* | (2006.01) |
| *A61K 9/48* | (2006.01) |
| *A61K 31/4545* | (2006.01) |
| *A61K 31/4402* | (2006.01) |
| *A61K 31/137* | (2006.01) |
| *A61K 9/08* | (2006.01) |
| *A61K 31/495* | (2006.01) |
| *A61K 31/485* | (2006.01) |
| *A61K 31/196* | (2006.01) |
| *A61K 9/24* | (2006.01) |

(52) U.S. Cl.
CPC ............. *A61K 9/0053* (2013.01); *A61K 9/08* (2013.01); *A61K 9/20* (2013.01); *A61K 9/48* (2013.01); *A61K 31/135* (2013.01); *A61K 31/137* (2013.01); *A61K 31/196* (2013.01); *A61K 31/404* (2013.01); *A61K 31/4402* (2013.01); *A61K 31/445* (2013.01); *A61K 31/4545* (2013.01); *A61K 31/47* (2013.01); *A61K 31/485* (2013.01); *A61K 31/495* (2013.01); *A61K 9/209* (2013.01); *A61K 9/2095* (2013.01)

(58) Field of Classification Search
CPC .... A61K 31/495; A61K 9/209; A61K 9/2095; A61K 9/2054
USPC .......................... 424/472, 464, 465; 514/255
See application file for complete search history.

(56) References Cited

U.S. PATENT DOCUMENTS

| 5,178,878 A | 1/1993 | Wehling et al. |
|---|---|---|
| 6,221,392 B1 | 4/2001 | Khankari et al. |
| 6,827,946 B2 * | 12/2004 | Hirsh .................. A61K 9/209 424/464 |
| 9,265,757 B2 * | 2/2016 | Nutalapati ........... A61K 31/445 |
| 2003/0118642 A1 | 6/2003 | Norman et al. |
| 2004/0253311 A1 | 12/2004 | Berlin et al. |
| 2008/0207593 A1 | 8/2008 | Heffernan et al. |
| 2016/0067180 A1 | 3/2016 | Westhusing et al. |
| 2016/0120811 A1 | 5/2016 | Nutalapati |

FOREIGN PATENT DOCUMENTS

CN    101716344 A    6/2010

OTHER PUBLICATIONS

Banerji et al., "Diphenhydramine versus nonsedating antihistamines for acute allergic reactions: A literature review"; 2007; Allergy Asthma Proc.; 28:418-426.

Cohen, "A Comparison of Methods for Assessing the Sedative Effects of Diphenhydramine on Skills Related to Car Driving"; 1984; Eur. J. Clin. Pharmacol.; 27: 477-482.

Day et al., "Onset of action and efficacy of terfenadine, astemizole, cetririzine, and loratadine for the relief of symptoms of allergic rhinitis", Annals of Allergy, Asthma, & Immunology (Aug. 1997), 79, 163-172.

Druce et al., "Brompheniramine, loratadine, and placebo in allergic rhinitis: a placebo-controlled comparative clinical trial", J Clin Pharmacol., Apr. 1998, 38(4), 382-389.

Huang et al., "Pharmacokinetics of Chlorpheniramine After Intravenous and Oral Administration in Normal Adults."; Eur J. Clinical Pharmacol;(1982)22:359-365.

Joseph M. Scavone, et al., "Pharmacokinetics and Pharmacodynamics of Diphenhydramine 25mg in Young and Elderly Volunteers." Journal of Clinical Pharmacology, 1998;38:603-609.

Kotzan et al., "Bioavailability of Regular and Controlled Released Chlorpheniramine Products."; Journal of Pharmaceutical Sciences; (1982);71:919.

Rumore., "Clinical pharmacokinetics of chlorpheniramine"; 1984; Drug Intelligence & Clinical Pharmacy; 18(9): 701-7; PubMed abstract; PMID: 6383755.

Vallner et al., "Blood Levels Following Multiple Oral Dosing of Chlorpheniramine Conventional and Controlled Release Preparations." Biopharmaceuticals & Drugs Disposition;(1982) vol. 3:95-104.

(Continued)

*Primary Examiner* — Kevin E Weddington
(74) *Attorney, Agent, or Firm* — Cantor Colburn LLP

(57) ABSTRACT

Combinations of a first generation antihistamine for a quick onset with a maintenance dosage amount of a second or third generation antihistamine, along with an additional active agent such as a decongestant, a cough suppressant (an antitussive), a leukotriene receptor antagonist, a 5-lipoxygenase inhibitor, a bronchodilator, an expectorant, or a combination thereof, are disclosed. Methods of using such combinations by concomitant administration, either in the form of a single composition or multiple compositions, are further disclosed.

11 Claims, No Drawings

(56) References Cited

OTHER PUBLICATIONS

Yacobi et al., "Evaluation of sustained-action of Chlorpheniramine Pseudoephedrine Dosage Form in Humans."; Journal of Pharmaceutical Sciences; (1980)69:1077.

* cited by examiner

ANTIHISTAMINE COMPOSITIONS, COMBINATIONS, AND USE THEREOF

BACKGROUND

Antihistamines find wide use in treating allergies by blocking the binding of histamine to histamine $H_1$-receptors and thereby suppressing symptoms such as a runny nose or watery eyes. So-called first generation antihistamines were developed that provided excellent reduction in the symptoms of rhinitis, however many of these early compounds induced a sedative effect in the patient, as they are nonselective for the $H_1$-receptor. Depending upon the time of day of administering a conventional recommended dose of a first generation antihistamine, the sedative effect may or may not be desired. For example, sedation would not be desired during the day while most patients need to be active and fully functional, often requiring awareness for daily activities such as working or driving a car.

Second and third generation antihistamines were subsequently designed to avoid the sedative effect exhibited in the earlier generation of compounds. These compounds were developed such that they do not cross the blood brain barrier and thus are selective for peripheral $H_1$ receptors outside of the central nervous system, thereby exhibiting a reduced sedative effect.

Although the second and third generation antihistamines avoid the sedative effect of the first generation antihistamines, they exhibit a lag from the time of administration to time when the patient starts to experience symptomatic relief. Several second generation antihistamines, such as terfenadine, astemizole, cetirizine, and loratadine, exhibit a lag time of several hours before onset of action (See Annals of Allergy, Asthma, & immunology (1997), 79, 163-172).

Thus, there remains a need in the art for antihistamine compositions and methods of administering antihistamines that provide rapid, sustained, and improved therapeutic effect while at the same time avoiding a sedative effect such that the administration can occur regardless of the time of day. There further remains a need for compositions combining antihistamines and an additional class of active agents to relieve other symptoms experienced by the patient, along with methods of administering such combinations.

SUMMARY

In an embodiment, an oral antihistamine combination comprises a first generation antihistamine in an attenuated dosage amount to provide a quick onset of action wherein a patient receiving the formulation experiences substantially no sedative effect; a second or third generation antihistamine in a maintenance dosage amount to provide continued antihistaminic effect; and an additional active agent, where the additional active agent is a decongestant, a cough suppressant (an antitussive), a leukotriene receptor antagonist, a 5-lipoxygenase inhibitor, a bronchodilator, an expectorant, or a combination thereof; and a pharmaceutically acceptable excipient, wherein at least the first generation antihistamine and the second or third generation antihistamine are formulated together into a single oral dosage form to be administered to a human patient regardless of the time of day.

In another embodiment, a method of orally administering an antihistamine combination comprises concomitantly orally administering to a human patient in need thereof a first generation antihistamine in an attenuated dosage amount to provide a quick onset of action wherein the patient experiences substantially no sedative effect; a second or third generation antihistamine in a maintenance dosage amount to provide continued antihistaminic effect; and an additional active agent, where the additional active agent is a decongestant, a cough suppressant (an antitussive), a leukotriene receptor antagonist, a 5-lipoxygenase inhibitor, a bronchodilator, an expectorant, or a combination thereof, wherein the administering can occur regardless of the time of day These and other embodiments, advantages and features of the present invention become clear when detailed description and examples are provided in subsequent sections.

DETAILED DESCRIPTION

Disclosed herein are therapeutic combinations comprising an attenuated dosage amount of a first antihistamine that is a first generation antihistamine to provide a quick onset of therapeutic action, a maintenance dosage amount of a second antihistamine that is a second or third generation antihistamine, and an additional active agent. The additional active agent may be a decongestant, a cough suppressant (an antitussive), a leukotriene receptor antagonist, a 5-lipoxygenase inhibitor, a bronchodilator, an expectorant, and the like, or a combination thereof. The combination provides quick onset of antihistamine activity and improves the efficacy of the combined antihistamines as they act synergistically with each other. The combination can be administered without regard to the time of day as the amount of first antihistamine will not induce a sedative effect or there will be substantially no sedative effect, but rather will provide early therapeutic effect during the lag time a patient may experience from the time of administration of a second or third generation antihistamine to when the patient experiences symptomatic relief.

Further disclosed herein are methods of administering to a patient in need thereof a combination comprising an attenuated dosage amount of a first antihistamine that is a first generation antihistamine to provide a quick onset of therapeutic action, a maintenance dosage amount of a second antihistamine that is a second or third generation antihistamine, and an additional active agent. The additional active agent may be a decongestant, a cough suppressant (an antitussive), a leukotriene receptor antagonist, a 5-lipoxygenase inhibitor, a bronchodilator, an expectorant, and the like, or a combination thereof. The combination provides quick onset and improves the efficacy of the antihistamines as the two act synergistically with each other. The method can be carried out without regard to the time of day as the amount of first antihistamine will not induce a sedative effect or there will be substantially no sedative effect, but rather will provide early therapeutic effect during the lag time a patient may experience from the time of administration of a second or third generation antihistamine to when the patient experiences symptomatic relief. For example, diphenhydramine, a first generation antihistamine, provides therapeutic effect within 15 to 30 minutes after administration, while it may take up to an hour or more for a patient to experience relief of symptoms using fexofenadine, as second generation antihistamine.

As used herein, "substantially no sedative effect" means the patient experiences such a minor sedative effect that it would not impair the patient's ability to operate machinery or automobiles or perform other mental or physical tasks requiring a high level of concentration.

The attenuated dosage amount of the first generation antihistamine is selected to avoid a sedative effect while at the same time providing adequate prophylactic and symptomatic treatment of seasonal or perennial allergic rhinitis, vasomotor rhinitis, or other respiratory allergies for the first 1-2 hours after dosage administration. The attenuated dosage amount of the first antihistamine is about 10 to about 96% of the conventional recommended dosage amount of the first generation antihistamine when used alone, specifically about 25 to about 80%, more specifically about 40 to about 65%, and yet more specifically about 50 to about 55% of the conventional recommended dosage amount. For example, a conventional recommended adult dose of diphenhydramine hydrochloride administered on its own is 25 milligrams (mg) to 50 mg. An attenuated dose for the present methods and compositions can be about 2.5 to about 23 mg when used in combination with a second/third generation antihistamine. Other examples are provided in the tables below.

|  | Name | Conventional recommended dose (adult) | Dose range for combination |
|---|---|---|---|
| 1st generation anti- histamine | Chlorpheniramine Maleate | 2 mg to 4 mg | 0.2 mg to 1.75 mg* |
|  | Diphenhydramine HCl | 25 mg to 50 mg | 2.5 mg to 23 mg* |
|  | Doxylamine Succinate | 6.25 mg to 12.5 mg | 0.625 mg to 6 mg* |
|  | Brompheniramine maleate | 4 mg | 0.4 mg to 3.6 mg* |
|  | Pheniramine maleate | 25 mg to 150 mg | 2.5 mg to 23 mg* |
|  | Clemastine fumarate | 2.68 mg | 0.268 mg to 2.4 mg* |
|  | Cyproheptadine HCl | 4 mg | 0.4 mg to 3.6 mg* |
|  | Promethazine HCl | 12.5 mg to 50 mg | 1.25 mg to 8.125 mg* |
|  | Triprolidine HCl | 2.5 mg to 10 mg | 0.25 mg to 1.625 mg* |
| 2nd/3rd generation anti- histamine | Cetirizine HCl | 10 mg | 9 to 10 mg |
|  | Loratadine | 10 mg | 9 to 10 mg |
|  | Fexofenadine HCl | 60 mg, 120 mg, 180 mg | 54 to 60 mg, 108 to 120 mg, 162 to 180 mg |
|  | Desloratadine | 2.5 mg, 5 mg | 2.25 to 2.5 mg, 4.5 to 5 mg |
|  | Levocetirizine dihydrochloride | 5 mg | 4.5 to 5 mg |
|  | Acrivastine | 8 mg | 7.2 to 8 mg |
|  | Terfenadine | 60 mg | 54 to 60 mg |

*Less than the conventional recommended dose.

The maintenance dosage amount of the second antihistamine, that is the second or third generation antihistamine, can be about 90 to 100% of the conventional recommended dosage amount, specifically 100%. Exemplary recommended dosage amounts are provided in the table above.

In one embodiment, a method of orally administering an antihistamine combination comprises concomitantly administering to a patient in need of antihistamine treatment a first generation antihistamine in an attenuated dosage amount to provide a quick onset of action while avoiding a sedative effect; a second or third generation antihistamine in a maintenance dosage amount to provide continued antihistaminic effect; and an additional active agent (e.g., a decongestant, a cough suppressant (an antitussive), a leukotriene receptor antagonist, a 5-lipoxygenase inhibitor, a bronchodilator, an expectorant, and the like, or a combination thereof) for additional symptomatic relief. As used herein, "concomitantly administering" means the first generation antihistamine, second/third generation antihistamine, and an additional active agent are administered simultaneously, or within fifteen minutes of one another, specifically within ten minutes, and more specifically within five minutes of one another.

In another embodiment, a method of using an antihistamine combination to treat a patient in need thereof comprises concomitantly administering to a patient in need of antihistamine treatment a first generation antihistamine in an attenuated dosage amount to provide a quick onset of action while avoiding a sedative effect; a second generation antihistamine in a maintenance dosage amount to provide continued antihistaminic effect; and an additional active agent (e.g., a decongestant, a cough suppressant (an antitussive), a leukotriene receptor antagonist, a 5-lipoxygenase inhibitor, a bronchodilator, an expectorant, and the like, or a combination thereof) for additional symptomatic relief.

In yet another embodiment, a method of treating a patient with an antihistamine combination comprises orally administering an attenuated dosage amount of a first generation antihistamine suitable for treatment of seasonal or perennial allergic rhinitis, vasomotor rhinitis, or other respiratory allergy to the patient who is concomitantly receiving administration of a second generation antihistamine and an additional active agent, wherein the attenuated dosage amount of first generation antihistamine is reduced compared to the conventional recommended daily dosage amount of the first generation antihistamine for treatment of seasonal or perennial allergic rhinitis, vasomotor rhinitis, or other respiratory allergy in the patient. Within this embodiment, the additional active agent can be a decongestant, a cough suppressant (an antitussive), a leukotriene receptor antagonist, a 5-lipoxygenase inhibitor, a bronchodilator, an expectorant, and the like, or a combination thereof. In one embodiment, the attenuated dosage amount of the first antihistamine is about 10 to about 96% of the conventional recommended daily dosage amount of the first generation antihistamine when used alone, specifically about 25 to about 80%, more specifically about 40 to about 65%, and yet more specifically about 50 to about 55% of the conventional recommended daily dosage amount.

In yet another embodiment, a method of using an antihistamine combination to treat a patient suffering from a condition treatable with an antihistamine comprises concomitantly administering to a patient in need of antihistamine treatment a first generation antihistamine in an attenuated dosage amount to provide a quick onset of action while avoiding a sedative effect; a second generation antihistamine in a maintenance dosage amount to provide continued antihistaminic effect; and an additional active agent (e.g., a decongestant, a cough suppressant (an antitussive), a leukotriene receptor antagonist, a 5-lipoxygenase inhibitor, a bronchodilator, an expectorant, and the like, or a combination thereof) for additional symptomatic relief.

Exemplary first generation antihistamines include brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof; specifically brompheniramine maleate, chlorpheneramine maleate, clemastine fumarate, cyproheptadine hydrochloride, diphenhydramine hydrochloride, doxylamine succinate, pheniramine maleate, promethazine hydrochloride, triprolidine hydrochloride, or a combination thereof.

Exemplary second and third generation antihistamines include acrivastine, astemizole, cetirizine, desloratadine, fexofenadine, levocetirizine, loratadine, mizolastine, terfenadine, a pharmaceutically acceptable salt thereof, or a combination thereof; specifically acrivastine, cetirizine hydrochloride, desloratadine, fexofenadine hydrochloride, levocetirizine dihydrochloride, loratadine, terfenadine, or a combination thereof.

Exemplary decongestants include pseudoephedrine, phenylephrine, a pharmaceutically acceptable salt thereof, or a combination thereof; specifically pseudoephedrine hydrochloride, pseudoephedrine sulfate, phenylephrine hydrochloride, or a combination thereof.

Exemplary cough suppressants (antitussive) include dextromethorphan, benzonatate, opioids (e.g. codeine, hydrocodone, and the like), a pharmaceutically acceptable salt thereof, or a combination thereof; specifically dextromethorphan hydrobromide, benzonatate, codeine phosphate, codeine sulfate, hydrocodone bitartrate, or a combination thereof.

Broncodilators include leukotriene receptor antagonists, beta-adrenergic agonists, anticholinergic, corticosteroids, mast cell stabilizers, and the like. Exemplary leukotriene receptor antagonists include montelukast, zafirlukast, pranlukast, a pharmaceutically acceptable salt thereof, or a combination thereof; specifically montelukast sodium, zafirlukast, and pranlukast.

Exemplary 5-lipoxygenase (also referred to as arachidonate 5-lipoxygenase) inhibitors include zileuton, meclofenamic acid, *Hypericum perforatum* (St. John's wort), a pharmaceutically acceptable salt thereof, or a combination thereof; specifically zileuton, meclofenamate sodium, and *Hypericum perforatum*.

The dosage amount of the additional active agent is a therapeutically effective amount. In an embodiment, the amount can be about 90 to 100% of the conventional recommended dosage amount, specifically 100%. Exemplary recommended dosage amounts of select decongestants, cough suppressants (antitussive), broncodilators, and 5-lipoxygenase inhibitors are provided in the table below.

| Name | Conventional recommended dose (adult) | Dose range for combination |
| --- | --- | --- |
| pseudoephedrine sulfate | 120 mg to 240 mg | 30 mg to 240 mg |
| pseudoephedrine HCl | 120 mg to 240 mg | 30 mg to 240 mg |
| phenylephrine hydrochloride | 20 mg to 40 mg | 20 mg to 40 mg |
| dextromethorphan hydrobromide | 60 mg to 120 mg | 60 mg to 120 mg |
| benzonatate | 300 mg to 600 mg | 300 mg to 600 mg |
| hydrocodone bitartrate | 40 mg to 60 mg | 40 mg to 60 mg |
| codeine sulfate | 90 mg to 360 mg | 90 mg to 360 mg |
| codeine phosphate | 90 mg to 360 mg | 90 mg to 360 mg |
| montelukast sodium | Adult: 10.4 mg (10 mg acid equivalent once a day) | 5 mg to 10 mg (acid equivalent) |
| zafirlukast | 20 mg to 40 mg | 10 mg to 40 mg |
| pranlukast | 225 mg to 450 mg | 225 mg to 450 mg |
| Zileuton | 600 mg to 2400 mg | 600 mg to 2400 mg |
| Meclofenamate sodium | 50 mg to 400 mg | 50 mg to 400 mg |

"Pharmaceutically acceptable salt" includes derivatives of the active agent, wherein the active agent is modified by making acid or base addition salts thereof, and further refers to pharmaceutically acceptable solvates, including hydrates, crystalline forms, non-crystalline forms, and polymorphs, of such salts. Examples of pharmaceutically acceptable salts include, but are not limited to, mineral or organic acid addition salts of basic residues such as amines; alkali or organic addition salts of acidic residues; and the like, or a combination thereof. The pharmaceutically acceptable salts include salts and the quaternary ammonium salts of the active agent. For example, acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, or a combination thereof. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; or a combination thereof.

A first antihistamine, a second antihistamine, and an additional active agent can each individually be formulated as separate, independent dosage forms to be administered to the patient. A "dosage form" means a unit of administration of an active agent. In an embodiment, the first antihistamine is formulated for immediate-release, while the second antihistamine and the additional active agent individually can be immediate-release, controlled-release, or a combination thereof.

In another embodiment, a first antihistamine, a second antihistamine, and an additional active agent are formulated together as a single dosage form to be administered together as a combination. In an alternative embodiment, two of a first antihistamine, a second antihistamine, and an additional active agent are formulated together as a single dosage form while the third is formulated as a separate, independent dosage form.

The antihistamines and additional active agent can be formulated for oral or buccal administration as a solid, liquid, or semisolid. "Oral dosage form" is meant to include a unit dosage form for oral administration. Exemplary solid oral and buccal dosage forms include tablets, capsules, pellets, films, and the like. Exemplary oral liquid dosage forms include solutions, suspensions, emulsions, and the like.

By "immediate-release" is meant a conventional or non-modified release in which greater than or equal to about 75% of the active agent is released within two hours of administration, specifically within one hour of administration, yet more specifically within 30 minutes of administration.

By "controlled-release" is meant a dosage form in which the release of the active agent is controlled or modified over a period of time, and does not include immediate-release. Controlled can mean, for example, extended/sustained-, delayed- or pulsed-release at a particular time.

Liquid Dosage Forms

The liquid dosage forms generally include one or more of the active agents (i.e. a first generation antihistamine, a second/third generation antihistamine, an additional active agent), and a liquid carrier. Additional optional ingredients include a suspending agent, a sweetener, a flavoring agent, a preservative, a pH adjusting agent, a colorant, or a combination thereof.

Any one of the first and second/third generation antihistamines and additional active agent can individually be present in the liquid composition in free form or in the form of a coated or uncoated granule, microtablet, pellet (as used herein "pellet" means a spherical granule prepared by extrusion and spheronization, and is equivalent to bead, spheroid, and microsphere), particle, a resin complex (e.g. ion exchange resin complex such as sodium polystyrene sulfonate), or other multiparticulate system. The coating can include film forming coating, a taste-masking coating, a controlled-release coating, and the like. The resin complex is suitable for providing extended release of the active agent, e.g. the additional active agent, for a once a day or other reduced administration regimen.

The liquid carrier can be water; glycerin; propylene glycol; a lower polyethylene glycol (e.g., polyethylene glycol 200, polyethylene glycol 300, polyethylene glycol 400, polyethylene glycol 540, polyethylene glycol 600, and the like); ethanol; propylene carbonate; or a combination thereof.

The liquid carrier can be present in the liquid composition in an amount of about 30 to about 98 weight percent (wt %) based on the total weight of the liquid composition, specifically about 40 to about 90 wt %, more specifically about 50 to about 80 wt %, and yet more specifically about 60 to about 70 wt %.

The suspending agent can be a carbomer, a cellulose derivative such as powdered cellulose, methylcellulose, a hydroxyl alkyl cellulose such as hydroxyethyl cellulose, hydroxypropyl cellulose, or hydroxypropyl methylcellulose, carboxy methyl cellulose calcium, carboxy methyl cellulose sodium, polyvinylpyrrolidone; a natural gum such as gum acacia, carrageenan, sodium alginate, gellam gum, gum ghatti, guar gum, locust bean gum, tragacanth, xanthan gum; or a combination thereof.

A sweetener can be included in the liquid composition to make the composition palatable and more pleasing to the patient and to mask the taste of the antihistamines. Exemplary sweeteners include sugar alcohols (or polyols), such as glycerol, sorbitol, xylitol, mannitol, galactitol, maltitol, hydrogenated isomaltulose (isomalt), lactitol, erythritol, glucitol, ribitol, or a combination thereof, sugar sweeteners generally include saccharides, such as mono-saccharides, di-saccharides and poly-saccharides such as sucrose (saccharose, sugar), dextrose, maltose, dextrin, maltodextrin, xylose, ribose, glucose (including liquid glucose), mannose, galactose, fructose (levulose), lactose, invert sugar, fructo oligo saccharide syrups, trehalose, tagatose, fucose, gulose, raffinose, ribulose, rufinose, stachyose, xylulose, adonose, amylase, arabinose, deoxyribose, corn syrup solids, such as high fructose corn syrup, or a combination thereof; artificial sweeteners such as soluble saccharin salts, i.e., sodium or calcium saccharin salts, the potassium salt of 3,4-dihydro-6-methyl-1,2,3-oxathiazine-4-one-2,2-dioxide (Acesulfame-K), the free acid form of saccharin, L-aspartic acid derived sweeteners, such as L-aspartyl-L-phenylalanine methyl ester (Aspartame), L-alphaaspartyl-N-(2,2,4,4-tetramethyl-3-thietanyl)-D-alaninamide hydrate (Alitame), N—[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, or a combination thereof; maltol; or a combination thereof.

The sweetener can be present in the liquid composition in an amount of about 0.1 to about 75 wt % based on the total weight of the liquid composition, specifically about 5 to about 50 wt %, and more specifically about 2.5 to about 25 wt %. The amount of sweetener can be determined by one of ordinary skill in the art without undue experimentation. The use of sensory panels to determine the acceptable sweetness of the liquid composition may be used.

The liquid composition may optionally further comprise a flavoring agent. Flavoring agents include those flavors known to one of ordinary skill in the art, such as natural flavors and artificial flavors. Suitable amounts of flavoring agent can be selected by one of ordinary skill in the art without undue experimentation. In one embodiment, the flavoring agent can be present in the liquid composition from about 0.1 to about 8.0 wt % based on the total weight of the liquid composition, specifically about 0.4 to about 6 wt %, and more specifically about 1.0 to about 3.0 wt %.

The liquid composition can further include a preservative to prevent the unwanted growth of bacteria, molds, fungi, or yeast. Examples of suitable preservatives include benzoic acid alkali metal salts (e.g., sodium benzoate), sorbic acid alkali metal salts (e.g., potassium sorbate), sodium erythorbate, sodium nitrite, calcium sorbate, butylated hydroxyanisole (BHA), butylated hydroxytoluene (BHT), parabens (e.g., lower alkyl esters of para-hydroxybenzoic acid), alkali metal salts of parabens including sodium and potassium salts of methyl-, ethyl-, propyl-, or butylparaben, or a combination thereof. Specific preservatives include sodium methylparaben, sodium propylparaben, and sodium butylparaben.

The preservative can be present in the liquid composition in an amount of about 0.001 to about 0.25 wt % based on the total weight of the composition, specifically about 0.0075 to about 0.20 wt %, and yet more specifically about 0.01 to about 0.15 wt %.

The liquid composition optionally further comprises a colorant conventional in the pharmaceutical art. Colorants can be used in amounts effective to produce a desired color for the composition. The colorants may include pigments, natural food colors and dyes suitable for pharmaceutical applications.

The liquid composition optionally further includes a pH adjusting agent to render the final liquid composition to a targeted pH. Suitable pH adjusting agents include pharmaceutically acceptable acids, bases, and their salts. Exemplary pH adjusting agents include alkali metal hydroxides (e.g., sodium hydroxide and potassium hydroxide), hydrochloric acid, alkali metal carbonates (e.g., sodium carbonate and potassium carbonate), carbonic acid, or a combination thereof. The pH adjusting agents can be used as solutions or suspensions in a pharmaceutically acceptable solvent. Suitable pharmaceutically acceptable solvents for use with the pH adjusting agent can include purified water, lower alkyl alcohols such as ethanol, a glycol, and the like, or a combination thereof.

The amount of pH adjusting agent can be any amount to result in a desired pH of the final liquid composition. Such amounts can be determined by one having ordinary skill in the art without undue experimentation.

In another embodiment, a first generation antihistamine, a second/third generation antihistamine, an additional active agent, or a combination thereof is formulated in a powder form, such as a sachet, to be suspended or reconstituted in a liquid carrier such as water or saliva. The powder form can be added to a glass of water with stirring or taken directly in the mouth where the ingredients are suspended in saliva. General components in the powder formulation include the antihistamines, a sweetener, and a suspending agent; optionally further comprising a flavorant, a colorant, a disintegrant, a combination thereof, and the like.

Solid Dosage Forms

The solid oral dosage form can be a monolithic matrix tablet or a layered tablet having two or more layers wherein each of the first and the second/third antihistamine and the additional active agent can be in separate layers or in the same layer; a capsule; a subunit form such as a plurality of granules, microtablets, minitablets, caplets, pellets (as used herein "pellet" means a spherical granule prepared by extrusion and spheronization, and is equivalent to bead, spheroid, and micro sphere), particles, active agent cores, resin complexes or other multiparticulate system.

In one embodiment, the first generation antihistamine, the second/third generation antihistamine, the additional active agent, or a combination thereof, is/are formulated as a solid oral dosage form comprising the antihistamine(s)/additional active agent and a pharmaceutically acceptable excipient. As used herein, "pharmaceutically acceptable excipient" means any other component added to the pharmaceutical formulation other than the active agent. Excipients may be added to facilitate manufacture, enhance stability, enhance product characteristics, enhance bioavailability, enhance patient acceptability, etc. Pharmaceutical excipients include carriers, fillers, binders, disintegrants, lubricants, glidants, granulating agents, compression aids, colors, sweeteners, preservatives, suspending agents, dispersing agents, film formers, flavorants, printing inks, buffer agents, pH adjusters, preservatives, and the like. In some instances, a single material will meet two or more of the foregoing general classifications.

Exemplary pharmaceutically acceptable excipients include fillers, such as a water insoluble filler, water soluble filler, or a combination thereof. The filler may be a water insoluble filler, such as carnauba wax, stearic acid, silicon dioxide, titanium dioxide, talc, alumina, starch, kaolin, polacrilin potassium, powdered cellulose, microcrystalline cellulose, sodium citrate, dicalcium phosphate, or a combination thereof. Exemplary water-soluble fillers include water soluble sugars and sugar alcohols, specifically lactose, glucose, fructose, sucrose, mannose, dextrose, galactose, the corresponding sugar alcohols and other sugar alcohols, such as mannitol, sorbitol, xylitol, or a combination thereof.

Exemplary binders include alginic acid, a carbomer, carboxymethylcellulose calcium, carboxymethylcellulose sodium, carrageenan, cellulose acetate phthalate, chitosan, ethyl cellulose, guar gum, hydroxyethyl cellulose, hydroxyethylmethyl cellulose, hydroxypropyl cellulose, hydroxypropyl methyl cellulose, methyl cellulose, microcrystalline cellulose, poloxamer, polyethylene oxide, polymethacrylates, povidone, a saccharide, starch, partially pregelatinized starch, and the like, or a combination thereof.

Exemplary disintegrants include alginic acid, carboxymethylcellulose calcium, carboxymethylcellulose sodium, cross-linked sodium carboxymethylcellulose (sodium croscarmellose), powdered cellulose, chitosan, croscarmellose sodium, crospovidone, guar gum, low substituted hydroxypropyl cellulose, methyl cellulose, microcrystalline cellulose, sodium alginate, sodium starch glycolate, partially pregelatinized starch, pregelatinized starch, starch, sodium carboxymethyl starch, and the like, or a combination thereof.

Exemplary lubricants include calcium stearate, magnesium stearate, glyceryl behenate, glyceryl palmitostearate, hydrogenated castor oil, light mineral oil, sodium lauryl sulfate, magnesium lauryl sulfate, sodium stearyl fumarate, stearic acid, zinc stearate, or a combination thereof.

Exemplary glidants include colloidal silica, amorphous silica, precipitated silica, talc, calcium phosphate tribasic, calcium silicate, magnesium silicate, magnesium trisilicate, or a combination thereof.

The solid oral dosage forms can be prepared using equipment and techniques known in the art for tableting included direct compression, granulation, capsule filling, pelletizing, and the like.

Orally Dispersible Tablet

The antihistamines, the additional active agent, or a combination of the antihistamines and the additional active agent can be formulated into a non-chewable, orally disintegrating tablet. These dosage forms can be made by methods known to those of ordinary skill in the art of pharmaceutical formulations. For example, Cima Labs has produced oral dosage forms including microparticles and effervescents, which rapidly disintegrate in the mouth and provide adequate taste-masking. Cima Labs has also produced a rapidly dissolving dosage form containing the active agent and a matrix that includes a nondirect compression filler and a lubricant. U.S. Pat. Nos. 5,178,878 and 6,221,392 provide teachings regarding orally disintegrating tablets.

An exemplary orally disintegrating tablet includes a mixture incorporating a water or saliva activated effervescent disintegration agent and the active agent. The mixture may be formulated as a tablet of a size and shape adapted for direct oral administration to a patient. The orally disintegrating tablet is substantially completely disintegrable upon exposure to water or saliva. The effervescent disintegration agent is present in an amount effective to aid in disintegration of the tablet, and to provide a distinct sensation of effervescence when the tablet is placed in the mouth of a patient.

The effervescent sensation is not only pleasant to the patient but also tends to stimulate saliva production, thereby providing additional water to aid in further effervescent action. Thus, once the tablet is placed in the patient's mouth, it will disintegrate rapidly and substantially completely without any voluntary action by the patient. Even if the patient does not chew the tablet, disintegration will proceed rapidly.

The term effervescent disintegration agent includes compounds which evolve gas. Exemplary effervescent disintegration agents evolve gas by means of chemical reactions which take place upon exposure of the effervescent disintegration agent to water or to saliva in the mouth. The bubble or gas generating reaction is most often the result of a reaction of a soluble acid source and an alkali metal carbonate or carbonate source. The reaction of these two general classes of compounds produces carbon dioxide gas upon contact with water included in saliva.

Such water activated materials may be kept in a generally anhydrous state with little or no absorbed moisture or in a stable hydrated form since exposure to water will prematurely disintegrate the tablet. The acid sources or acid may be those which are safe for human consumption and may generally include food acids, acid anhydrides and acid salts. Food acids include citric acid, tartaric acid, malic acid, fumaric acid, adipic acid, and succinic acids, etc. Because these acids are directly ingested, their overall solubility in water is less important than it would be if the effervescent tablet formulations were intended to be dissolved in a glass of water. Acid anhydrides and acid of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate, amorphous calcium carbonate, or a combination thereof.

Where the effervescent agent includes two mutually reactive components, such as an acid source and a carbonate source, in one embodiment both components react substantially completely. Therefore, an equivalent ratio of components which provides for equal equivalents is selected. For example, if the acid used is diprotic, then either twice the amount of a mono-reactive carbonate base, or an equal amount of a di-reactive base is used for complete neutralization to be realized. However, the amount of either acid or carbonate source may exceed the amount of the other component. This may be useful to enhance taste or performance of a tablet containing an overage of either component. In this case, it is acceptable that the additional amount of either component may remain unreacted.

In general, the amount of effervescent disintegration agent useful for the formation of orally disintegrating tablets is about 5 wt % to about 50 wt % based on the total weight of the final dosage form, specifically about 15 wt % and about 30 wt %, and more specifically about 20 wt % to about 25 wt %.

Other types of orally disintegrating tablets can be prepared without an effervescent agent by using a spray dried carbohydrate or sugar alcohol excipients (e.g. sorbitol, mannitol, xylitol, or a combination thereof, and the like), optionally combined with a disintegrant (e.g. the disintegrant is selected from crospovidone, croscarmellose, sodium starch glycolate, pregelatinized starch, partially pregelatinized starch, or a combination thereof, and the like), or a glidant (e.g. colloidal silica, silica gel, precipitated silica, or a combination thereof, and the like). Suitable orally disintegrating tablets can be found in U.S. Patent Application Publication US20030118642 A1 to Norman et al. incorporated herein by reference in its entirety.

Orally disintegrating tablets can be manufactured by well-known tableting procedures. In common tableting processes, the material which is to be tableted is deposited into a cavity, and one or more punch members are then advanced into the cavity and brought into intimate contact with the material to be pressed, whereupon compressive force is applied. The material is thus forced into conformity with the shape of the punches and the cavity.

The orally disintegrating tablets typically rapidly disintegrate when orally administered. By "rapid", it is understood that the tablets disintegrate in the mouth of a patient in less than about 7 minutes, and specifically between about 30 seconds and about 5 minutes, specifically the tablet dissolves in the mouth between about 45 seconds and about 2 minutes. Disintegration time in the mouth can be measured by observing the disintegration time of the tablet in water at about 37° C. The tablet is immersed in the water without forcible agitation. The disintegration time is the time from immersion to substantially complete dispersion of the tablet as determined by visual observation. As used herein, the term "complete disintegration" of the tablet does not require dissolution or disintegration of the subunits or other discrete inclusions. In one embodiment, disintegration can be determined by USP 32 (Test <701>).

Films

In another embodiment, the antihistamines, the additional active agent, or a combination of the antihistamines and the additional active agent are formulated into an orally dissolving film (also referred to as a strip), which rapidly dissolves in the mouth to release the active agent(s) contained in the strip. The orally dissolving strips generally comprise a water soluble polymer and the antihistamine, the combination of antihistamine, the additional active agent, or any combination thereof. Exemplary classes of water soluble polymers include water soluble cellulosic polymers, water soluble synthetic polymers, water soluble natural gums and polymers or derivatives thereof, or a combination thereof. Exemplary water soluble cellulosic polymers include hydroxypropyl cellulose, hydroxypropylmethyl cellulose, hydroxyethyl cellulose, carboxymethyl cellulose, or a combination thereof. Exemplary water soluble natural gums and polymers include amylose, dextran, casein, pullulan, gelatin, pectin, agar, carrageenan, xanthan gum, tragacanth, guar gum, acacia gum, arabic gum, sodium alginate, zein, or a combination thereof. Exemplary water soluble synthetic polymers include polyethylene glycol, polyethylene oxide, polyvinyl pyrrolidone, polyvinyl alcohol, carboxyvinyl polymers, water soluble polyacrylic acid/acrylate, or a combination thereof.

The water soluble polymer may be present in amounts of about 20 to about 95 wt %, specifically about 30 to about 85, and more specifically about 40 to about 75 wt % based on the total weight of the orally dissolving strip.

The orally dissolving strip can further optionally comprise a plasticizer in addition to the water soluble polymer and active agent. Exemplary plasticizers include propylene glycol, glycerin, glycerol, monoacetin, diacetin, triacetin, dimethyl phthalate, diethyl phthalate, dibutyl phthalate, dibutyl sebacate, triethyl titrate, tributyl citrate, triethyl citrate, triethyl acetyl citrate, castor oil, acetylated monoglycerides, sorbitol, or a combination thereof. The plasticizer may be present in amounts of about 0 to about 20, specifically about 1 to about 15, and more specifically about 5 to about 10 wt % based on the total weight of the orally dissolving strip.

The orally dissolving strip can further optionally comprise an emulsifying agent in addition to the water soluble polymer and active agent. Exemplary emulsifying agents include polyvinyl alcohol, a sorbitan esters, a cyclodextrin, benzyl benzoate, glyceryl monostearate, a polyoxyethylene alkyl ether, a polyoxyethylene stearate, poloxamer, a polyoxyethylene castor oil derivative, a hydrogenated vegetable oil, a polysorbate, or a combination thereof.

The emulsifying agent may be present in amounts of about 0 to about 20, specifically about 1 to about 15, and more specifically about 5 to about 10 wt % based on the total weight of the orally dissolving strip.

The orally dissolving strip can further optionally comprise a flavorant or sweetener in addition to the water soluble polymer and active agent. Exemplary sweeteners include sugar, a monosaccharide, an oligosaccharide, aldose, ketose, dextrose, maltose, lactose, glucose, fructose, sucrose, a sugar polyol (e.g., mannitol, xylitol, sorbitol, erythritol, and the like), artificial sweeteners (e.g., acesulfame potassium, sucralose, aspartame, saccharin, sodium saccharin, and the like) or a combination thereof. The sweetener may be present in amounts of about 0 to about 20, specifically about 1 to about 15, and more specifically about 5 to about 10 wt % based on the total weight of the orally dissolving strip.

In some embodiments, the orally dissolving formulations of the present invention may comprise an additional excipient. Suitable additional excipients include, but are not limited to, microcrystalline cellulose, colloidal silicon dioxide, talc, starch, or a combination thereof. Other optional components that can be used to prepare the orally dissolving strip include a filler/diluent, a surfactant, a disintegrating agent, an antifoaming agent, an antioxidant, a buffering agent, a colorant, or a combination thereof.

In one embodiment, the orally dissolving strip exhibits a drug loading of not more than 50% w/w of the film.

Exemplary orally dissolving strips will comprise about 0.01 to about 50 mg of active agent per strip. In another embodiment, the orally dissolving strip has a thickness of about 0.1 to about 5.0 millimeters, specifically about 0.3 to about 4.0 and yet more specifically about 0.5 to about 2.5 millimeters. In another embodiment the orally dissolving strip has a surface area of about 1.0 to about 6.0, specifically about 1.2 to about 4.0 and yet more specifically about 1.5 to about 2.0 square centimeters.

The orally dissolving strip once placed in the oral cavity may dissolve after less than about 60 seconds, specifically less than 30 seconds, and yet more specifically less than about 20 seconds.

A solvent can be used in the process to prepare the orally dissolving strip, including water, ethanol, 1-butanol, 2-butanol, 2-ethoxyethanol, ethyl acetate, methyl acetate, 3-methyl-1-butanol, methylethyl ketone, 2-methyl-1-propanol, isobutyl acetate, isopropyl acetate ethyl ether, tert-butylmethyl ether acetone, or a combination thereof. The solvent is used for processing and then removed to result in the final product.

Methods of preparing orally dissolving strips involve solvent casting and film coating. The active agent is mixed with film-forming excipients and solvents such as water, ethanol, and the like. A thin coating of the mixture is cast on a moving, inert substrate and the coated substrate is moved through a drying oven to evaporate the solvent before die-cutting the dried film into strips. Another method involves hot-melt extrusion, by melting an active agent and excipient polymer blend which is then extruded through a die under molten conditions. The thin film is then cooled to room temperature and die-cut into strips.

Kits

Also included herein are pharmaceutical kits comprising one multiple use, or a plurality of single use containers or units containing the antihistamine dosage forms as described herein. The kits may further comprise one or more conventional pharmaceutical kit components, such as, for example, one or more containers to aid in facilitating compliance with a particular dosage regimen; one or more carriers; printed instructions, either as inserts or as labels, indicating quantities of the components to be administered, or guidelines for administration. Exemplary kits can be in the form of bubble or blister pack cards, optionally arranged in a desired order for a particular dosing regimen. Suitable blister packs that can be arranged in a variety of configurations to accommodate a particular dosing regimen are well known in the art or easily ascertained by one of ordinary skill in the art.

Those forms existing as liquids (e.g solution, emulsion, or suspension) can be packaged for convenient dosing in prepackaged, single use containers, or in containers comprising multiple doses.

In an embodiment, the combination can be administered to a patient in need of prophylactic and symptomatic treatment of seasonal or perennial allergic rhinitis, vasomotor rhinitis, or other respiratory allergies. Seasonal allergic rhinitis may be due to allergens such as ragweed, grass and tree pollens. Perennial allergic rhinitis may be due to allergens such as dust mites, animal dander and molds. Symptoms treated may include sneezing, rhinorrhea, postnasal discharge, nasal pruritus, ocular pruritus, tearing, and redness of the eyes. Patients may include mammals, especially humans, including human adults, geriatric, or pediatric patients.

The following contains a non-limiting embodiments.

Embodiment 1. An oral antihistamine combination, comprising a first generation antihistamine in an attenuated dosage amount to provide a quick onset of action wherein a patient receiving the formulation experiences substantially no sedative effect; a second or third generation antihistamine in a maintenance dosage amount to provide continued antihistaminic effect; and an additional active agent, where the additional active agent is a decongestant, a cough suppressant (an antitussive), a leukotriene receptor antagonist, a 5-lipoxygenase inhibitor, a bronchodilator, an expectorant, or a combination thereof; and a pharmaceutically acceptable excipient, wherein at least the first generation antihistamine and the second or third generation antihistamine are formulated together into a single oral dosage form to be administered to a human patient regardless of the time of day.

Embodiment 2. The combination of Embodiment 1, wherein the first generation antihistamine, the second or third generation antihistamine, and the additional active agent are formulated together into a single oral dosage form to be administered to a human patient regardless of the time of day.

Embodiment 3. The combination of any one of Embodiments 1 or 2, wherein the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof; the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; the decongestant is pseudoephedrine, phenylephrine, a pharmaceutically acceptable salt thereof, or a combination thereof; the cough suppressant is dextromethorphan, benzonatate, an opioid, a pharmaceutically acceptable salt thereof, or a combination thereof; the leukotriene receptor antagonist is montelukast, zafirlukast, pranlukast, a pharmaceutically acceptable salt thereof, or a combination thereof, the 5-lipoxygenase inhibitor is zileuton, meclofenamic acid, *Hypericum perforatum* (St. John's wort), a pharmaceutically acceptable salt thereof, or a combination thereof; and the bronchodilator is leukotriene receptor antagonists, beta-adrenergic agonists, anticholinergic, corticosteroids, mast cell stabilizers, a pharmaceutically acceptable salt thereof, or a combination thereof.

Embodiment 4. The combination of any one of Embodiments 1-3, wherein the first generation antihistamine is brompheniramine maleate in an attenuated dosage amount of about 0.4 mg to about 3.6 mg, about 0.5 mg to about 3.0 mg, about 0.75 mg to about 2.5 mg, or about 1.0 mg to about 2.0 mg; chlorpheneramine maleate in an attenuated dosage amount of about 0.2 mg to about 1.75 mg, about 0.5 mg to about 1.5 mg, or about 0.75 mg to about 1.0 mg; clemastine fumarate in an attenuated dosage amount of about 0.268 mg to about 2.4 mg, or about 0.3 mg to about 2.0 mg, or about 0.7 mg to about 1.5 mg; cyproheptadine hydrochloride in an attenuated dosage amount of about 0.4 mg to about 3.6 mg, about 0.6 mg to about 3.0 mg, or about 1.0 mg to about 2.0 mg; diphenhydramine hydrochloride in an attenuated dosage amount of about 2.5 mg to about 23 mg, about 3.5 mg to about 15 mg, about 4.0 mg to about 10 mg, or about 5.0 mg to about 6.25 mg; doxylamine succinate in an attenuated dosage amount of about 0.625 mg to about 6.0 mg, about 1.0 mg to about 4.0 mg, about 1.5 mg to about 3.0 mg, or about 2.0 mg to about 2.5 mg; pheniramine maleate in an attenuated dosage amount of about 2.5 mg to about 23 mg, about 5.0 mg to about 20.0 mg, or about 10.0 mg to about 15.0 mg; promethazine hydrochloride in an attenuated dosage amount of about 1.25 mg to about 8.125 mg, about 2.0 mg to about 6.0 mg, or about 3.0 mg to about 5.0 mg; triprolidine hydrochloride in an attenuated dosage amount of about 0.25 mg to about 1.625 mg, about 0.5 mg to about 1.5 mg, or about 0.75 mg to about 1.0 mg; or a combination thereof; and the second or third generation antihistamine is acrivastine in an amount of about 7.2 mg to about 8.0 mg; cetirizine hydrochloride in an amount of about 9.0 mg to about 10 mg; desloratadine in an amount of about 2.25 to about 5 mg, about 2.25 to about 2.5 mg, or about 4.5 mg to about 5 mg; fexofenadine hydrochloride in an amount of about 54 mg to about 180 mg, about 54 mg to about 60 mg, or about 108 mg to about 120 mg, or about 162 mg to about 180 mg; levocetirizine dihydrochloride in an amount of about 4.5 mg to about 5 mg, loratadine in an amount of about 9.0 mg to about 10 mg, terfenadine in an amount of about 54 mg to about 60 mg, or a combination thereof.

Embodiment 5. The combination of any one of Embodiments 1-4, wherein at least the first generation antihistamine and the second or third generation antihistamine are formulated together into a single oral dosage form, wherein the dosage form is a tablet, a capsule, a pellet, a film, a solution, a suspension, an emulsion, a powder, or a granule.

Embodiment 6. The combination of any one of Embodiments 1-5, to be administered once a day or twice a day.

Embodiment 7. The combination of any one of Embodiments 1-6, wherein the first generation antihistamine when administered to a patient provides therapeutic prophylactic and symptomatic treatment of seasonal or perennial allergic rhinitis, vasomotor rhinitis, or other respiratory allergies for the first 1 hour after administration or for the first 2 hours after administration.

Embodiment 8. The combination of any one of Embodiments 1-7 for pediatric use.

Embodiment 9. The combination of any one of Embodiments 1-8, wherein the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof; the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; and the decongestant is pseudoephedrine, phenylephrine, a pharmaceutically acceptable salt thereof, or a combination thereof.

Embodiment 10. The combination of any one of Embodiments 1-9, wherein the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof; the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; and the leukotriene receptor antagonist is montelukast, zafirlukast, pranlukast, a pharmaceutically acceptable salt thereof, or a combination thereof.

Embodiment 11. A method of orally administering an antihistamine combination, comprising: concomitantly orally administering to a human patient in need thereof a first generation antihistamine in an attenuated dosage amount to provide a quick onset of action wherein the patient experiences substantially no sedative effect; a second or third generation antihistamine in a maintenance dosage amount to provide continued antihistaminic effect; and an additional active agent, where the additional active agent is a decongestant, a cough suppressant (an antitussive), a leukotriene receptor antagonist, a 5-lipoxygenase inhibitor, a bronchodilator, an expectorant, or a combination thereof, wherein the administering can occur regardless of the time of day.

Embodiment 12. The method of Embodiment 11, wherein the first generation antihistamine, the second or third generation antihistamine, and the additional active agent are formulated as a single oral dosage form; each formulated as an individual oral dosage form; or two of the first generation antihistamine, the second or third generation antihistamine, and the additional active agent are formulated as a single oral dosage form and the third is formulated as an individual dosage form.

Embodiment 13. The method of Embodiment 12, wherein each oral dosage form is individually a tablet, a capsule, a pellet, a film, a solution, a suspension, an emulsion, a powder, or a granule.

Embodiment 14. The method of any one of Embodiments 11-13, wherein the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof, the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; the decongestant is pseudoephedrine, phenylephrine, a pharmaceutically acceptable salt thereof, or a combination thereof; the cough suppressant is dextromethorphan, benzonatate, an opioid, a pharmaceutically acceptable salt thereof, or a combination thereof; the leukotriene receptor antagonist is montelukast, zafirlukast, pranlukast, a pharmaceutically acceptable salt thereof, or a combination thereof, the 5-lipoxygenase inhibitor is zileuton, meclofenamic acid, *Hypericum perforatum* (St. John's wort), a pharmaceutically acceptable salt thereof, or a combination thereof; and the bronchodilator is leukotriene receptor antagonists, beta-adrenergic agonists, anticholinergic, corticosteroids, mast cell stabilizers, a pharmaceutically acceptable salt thereof, or a combination thereof.

Embodiment 15. The method of any one of Embodiments 11-14, wherein the first generation antihistamine is brompheniramine maleate in an attenuated dosage amount of about 0.4 mg to about 3.6 mg, about 0.5 mg to about 3.0 mg, about 0.75 mg to about 2.5 mg, or about 1.0 mg to about 2.0 mg; chlorpheneramine maleate in an attenuated dosage amount of about 0.2 mg to about 1.75 mg, about 0.5 mg to about 1.5 mg, or about 0.75 mg to about 1.0 mg; clemastine fumarate in an attenuated dosage amount of about 0.268 mg to about 2.4 mg, or about 0.3 mg to about 2.0 mg, or about 0.7 mg to about 1.5 mg; cyproheptadine hydrochloride in an attenuated dosage amount of about 0.4 mg to about 3.6 mg, about 0.6 mg to about 3.0 mg, or about 1.0 mg to about 2.0 mg; diphenhydramine hydrochloride in an attenuated dosage amount of about 2.5 mg to about 23 mg, about 3.5 mg to about 15 mg, about 4.0 mg to about 10 mg, or about 5.0 mg to about 6.25 mg; doxylamine succinate in an attenuated dosage amount of about 0.625 mg to about 6.0 mg, about 1.0 mg to about 4.0 mg, about 1.5 mg to about 3.0 mg, or about 2.0 mg to about 2.5 mg; pheniramine maleate in an attenuated dosage amount of about 2.5 mg to about 23 mg, about 5.0 mg to about 20.0 mg, or about 10.0 mg to about 15.0 mg; promethazine hydrochloride in an attenuated dosage amount of about 1.25 mg to about 8.125 mg, about 2.0 mg to about 6.0 mg, or about 3.0 mg to about 5.0 mg; triprolidine hydrochloride in an attenuated dosage amount of about 0.25 mg to about 1.625 mg, about 0.5 mg to about 1.5 mg, or about 0.75 mg to about 1.0 mg; or a combination thereof; and the second or third generation antihistamine is acrivastine in an amount of about 7.2 mg to about 8.0 mg; cetirizine hydrochloride in an amount of about 9.0 mg to about 10 mg; desloratadine in an amount of about 2.25 to about 5 mg, about 2.25 to about 2.5 mg, or about 4.5 mg to about 5 mg; fexofenadine hydrochloride in an amount of about 54 mg to about 180 mg, about 54 mg to about 60 mg, or about 108 mg to about 120 mg, or about 162 mg to about 180 mg; levocetirizine dihydrochloride in an amount of about 4.5 mg to about 5 mg, loratadine in an amount of about 9.0 mg to about 10 mg, terfenadine in an amount of about 54 mg to about 60 mg, or a combination thereof.

Embodiment 16. The method of any one of Embodiments 11-15, to be administered once a day or twice a day.

Embodiment 17. The method of any one of Embodiments 11-16, wherein the first generation antihistamine when administered to a patient provides therapeutic prophylactic and symptomatic treatment of seasonal or perennial allergic rhinitis, vasomotor rhinitis, or other respiratory allergies for the first 1 hour after administration or for the first 2 hours after administration.

Embodiment 18. The method of any one of Embodiments 11-17 for pediatric use.

Embodiment 19. The method of any one of Embodiments 11-18, wherein the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof; the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; and the decongestant is pseudoephedrine, phenylephrine, a pharmaceutically acceptable salt thereof, or a combination thereof.

Embodiment 20. The method of any one of Embodiments 11-19, wherein the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof; the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; and the leukotriene receptor antagonist is montelukast, zafirlukast, pranlukast, a pharmaceutically acceptable salt thereof, or a combination thereof.

The following non-limiting examples further illustrate the various embodiments described herein.

EXAMPLES

Example 1

Immediate Release Tablets/Capsules

Immediate release tablets or capsules are prepared using diphenhydramine HCl as the first antihistamine, fexofenedine HCl as the second antihistamine, and montelukast sodium or zafirlukast as the additional active agent. The formulation is provided in Table 1.

TABLE 1

| Ingredients | Milligram/tablet or capsule | Milligram/tablet or capsule |
|---|---|---|
| Fexofenedine HCl | 60.0 to 180.0 | 60.0 to 180.0 |
| Diphenhydramine HCl | 2.5 to 10.0 | 2.5 to 10.0 |
| Montelukast sodium | 5.2 to 10.4 | — |
| Zafirlukast | — | 10 to 40 |
| PEG 3350 | 32.5 | 32.5 |
| Croscarmellose Sodium (Ac-Di-Sol) | 15.0 | 15.0 |
| Partially pregelatinized maize starch (Starch 1500 ®) | 25.0 | 25.0 |
| Magnesium Stearate | 2.5 | 2.5 |
| Total | 142.7 to 275.4 | 147.5 to 305.0 |

Fexofenedine HCl, diphenhydramine HCl, montelukast sodium, and PEG 3350 are charged into a blender and mixed. Ac-Di-Sol and Starch 1500 are then added to the blender and mixed. Magnesium stearate is passed through a # 30 mesh screen and added to the blender and mixed to form a final blend. The final blend can be compressed into tablets or filled into capsules.

One tablet or capsule of Example 1 can be administered to a patient once or twice a day.

Example 2

Chewable Tablets

Chewable tablets are prepared using chlorpheneramine maleate as the first antihistamine, loratadine as the second antihistamine, and pseudoephedrine HCl, pseudoephedrine sulfate, or phenylephrine HCl as the additional active agent. The formulation is provided in Table 2.

TABLE 2

| Ingredients | Milligram/tablet | Milligram/tablet |
|---|---|---|
| Loratadine | 9.0 to 10.0 | 9.0 to 10.0 |
| Chlorpheneramine Maleate | 0.2 to 1.75 | 0.2 to 1.75 |
| Pseudoephedrine HCl or Pseutoephedrine sulfate | 30 | — |
| Phenylephrine HCl | — | 5.0 |
| Microcrystalline cellulose | 38.50 | 38.50 |
| Mannitol | 45.00 | 45.00 |
| Silicon dioxide | 2.00 | 2.00 |
| Citric acid | 1.00 | 1.00 |
| Magnesium Stearate | 1.00 | 1.00 |
| Aspartame | 0.10 | 0.10 |
| Color | 0.10 | 0.10 |
| Flavor | 0.50 | 0.50 |
| Total | 127.4 to 129.95 | 102.4 to 104.95 |

Color is passed through a # 30 mesh screen using microcrystalline cellulose. Loratadine, chlorpheneramine maleate, the additional active agent, mannitol and the screened ingredients are charged into a blender and mixed. Silicon dioxide, citric acid, aspartame and flavor are passed through a # 30 mesh screen and then added to the blender and mixed. Magnesium stearate that has been screened through a # 30 mesh is then added to the blender and mixed to form a final mixture. The final mixture is then compressed into chewable tablets.

One chewable tablet of Example 2 can be administered to a patient once a day.

Example 3

Oral Solution

An oral solution is prepared where each 5 milliliters (ml) contains 1 mg of chlorpheneramine maleate as the first antihistamine, 5 mg of cetirizine HCl as the second antihistamine, and 10 mg of dextromethorphan hydrobromide as the additional active agent. The oral solution formulation is shown in Table 3.

TABLE 3

| Ingredients | Gram/batch |
| --- | --- |
| Cetirizine HCl | 0.10 |
| Chlorpheneramine Maleate | 0.02 |
| Dextromethorphan HBr | 0.20 |
| Citric acid anhydrous, USP/NF | 0.30 |
| Glycerin, USP | 8.00 |
| Propylene glycol | 18.38 |
| PEG 400, NF | 1.00 |
| Sodium benzoate, NF | 0.20 |
| Sugar, NF | 20.50 |
| Sodium saccharin | 0.30 |
| Soduim citrate, USP/NF | 0.40 |
| Color | 0.10 |
| Flavor | 0.20 |
| Purified water | 50.20 |
| Total Weight | 100.00 |

The oral solution is prepared by dissolving citric acid and sodium citrate in water. Sodium saccharin and sodium benzoate are then added and dissolved. Cetirizine HCl, chlorpheneramine maleate, and dextromethorphan HBr are then added and dissolved by mixing for 10 minutes. Sugar is then added and mixed for 30 minutes to dissolve. Propylene glycol and PEG 400 are then added and mixed for 5 minutes. Glycerin is then added and mixed for 10 minutes. Colors and flavors are dissolved in a small amount of water and then added to the main container with mixing. Any remaining water is added to the mixture and mixed for 25 minutes to form the oral solution.

A 5 milliliter dose of the oral solution of Example 3 can be administered to a patient as a single daily dose.

Example 4

Extended Release Oral Solution

An oral solution is prepared where each 5 milliliters (ml) contains 1 mg of chlorpheneramine maleate as the first antihistamine, 5 mg of cetirizine HCl as the second antihistamine, and 30 mg of dextromethorphan hydrobromide as the additional active agent which is released over a 12-hour period. The extended release oral solution formulation is shown in Table 4.

TABLE 4

| Ingredients | Gram/batch |
| --- | --- |
| Cetirizine HCl | 0.1 |
| Chlorpheneramine Maleate | 0.02 |
| Coated Dextromethorphan HBr resin complex | 1.2 |
| Citric acid anhydrous, USP/NF | 0.3 |
| Glycerin, USP | 8 |
| Propylene glycol | 18.38 |
| PEG 400, NF | 1 |

TABLE 4-continued

| Ingredients | Gram/batch |
| --- | --- |
| Sodium benzoate, NF | 0.2 |
| Sugar, NF | 20.5 |
| Sodium saccharin | 0.3 |
| Soduim citrate, USP/NF | 0.4 |
| Color | 0.1 |
| Flavor | 0.2 |
| Purified water | 49.3 |
| Total Weight | 100 |

The oral solution is prepared by dissolving citric acid and sodium citrate in water. Sodium saccharin and sodium benzoate are then added and dissolved. Cetirizine HCl and chlorpheneramine maleate are dissolved by mixing for 10 minutes. Coated dextromethorphan HBr resin complex pellets are then added and dispersed by mixing for 10 minutes. Sugar is then added and mixed for 30 minutes to dissolve. Propylene glycol and PEG 400 are then added and mixed for 5 minutes. Glycerin is then added and mixed for 10 minutes. Colors and flavors are dissolved in a small amount of water and then added to the main container with mixing. Any remaining water is added to the mixture and mixed for 25 minutes to form the oral solution.

A 5 milliliter dose of the oral solution of Example 4 can be administered to a patient as a single daily dose.

Example 5

Orally Disintegrating Tablet

An orally disintegrating tablet is prepared with chlorpheneramine maleate as the first antihistamine, loratadine as the second antihistamine, and meclofenamate sodium as the additional active agent (Table 6.).

TABLE 5

| Ingredients | Milligram/tablet |
| --- | --- |
| Loratadine | 9.0 to 10.0 |
| Chlorpheneramine Maleate | 0.2 to 1.75 |
| Meclofenamate sodium | 53.7 to 107.4* |
| Granulated mannitol (Pearlitol ® SD100) | 70.2 |
| Crosslinked Polyvinylpyrrolidone (Plasdone XL 10) | 10.0 |
| Peppermint flavor | 3.0 |
| Stearic acid | 5.0 |
| Total | 151.1 to 207.4 |

*Equivalent to 50 to 100 mg meclofenamic acid.

Loratadine, chlorpheneramine maleate, meclofenamate sodium and Pearlitol SD100 are charged into a blender and mixed. Plasdone XL10 and peppermint flavor are passed through a # 30 mesh screen and added to the blender and mixed. Stearic acid is passed through a # 30 mesh screen, added to the blender and mixed to form a final blend. The final blend is compressed into tablets.

One orally disintegrating tablet of Example 5 can be administered to a patient once a day.

Example 6

Bilayer Tablets (Immediate Release)

A bilayer tablet is formed having the first antihistamine brompheniramine maleate in one layer and second antihistamine cetirizine HCl in a second layer (Table 6).

TABLE 6

| | Milligram/tablet |
|---|---|
| First Layer Ingredients | |
| Brompheniramine maleate | 0.2 to 1.75 |
| Microcrystalline cellulose | 39.25 to 40.8 |
| Lactose Fast Flo ® | 45.00 |
| Polyvinylpyrrolidone (Plasdone K29/32) | 10.00 |
| Crosslinked Polyvinylpyrrolidone (Plasdone XL 10) | 3.00 |
| Magnesium Stearate | 1.00 |
| Total | 100.00 |
| Second Layer Ingredients | |
| Cetirizine HCl | 9.00 to 10.00 |
| Microcrystalline cellulose | 37.00 to 38.00 |
| Lactose Fast Flo ® | 45.00 |
| Silicon dioxide | 2.00 |
| Croscarmellose Sodium (Ac-Di-Sol) | 5.00 |
| Magnesium Stearate | 1.00 |
| Total | 100.00 |

The first layer is formed by charging brompheniramine maleate, microcrystalline cellulose, and Lactose Fastflo into a blender and mixed. Plasdone K29/32 and Plasdone XL10 are passed through a # 30 mesh screen, added to the blender and mixed. Magnesium stearate is passed through a # 30 mesh screen and added to the blender and mixed to form a final first layer blend.

The second layer is formed by charging cetirizine HCl, microcrystalline cellulose, and Lactose Fastflo into a second blender and mixed. Silicon dioxide, and Ac-Di-Sol are passed through a # 30 mesh screen, added to the blender and mixed. Magnesium stearate is then passed through a # 30 mesh screen, added to the blender and mixed to form a final second layer blend. Bilayer tablets are formed by compressing 100 mg of the final first layer blend and 100 mg of the final second layer blend.

One bilayer tablet of Example 6 can be administered to a patient once a day along with a 600 mg zileuton tablet or capsule as a separate dosage form.

Example 7

Bilayer Tablets (Extended Release)

A bilayer tablet is formed having the first antihistamine brompheniramine maleate and second antihistamine cetirizine HCl in the first immediate release layer and Pseudoephedrine HCl in a second extended release layer (Table 7).

TABLE 7

| | Milligram/tablet |
|---|---|
| First Layer Ingredients | |
| Brompheniramine maleate | 0.2 to 1.75 |
| Cetirizine HCl | 9.00 to 10.00 |
| Microcrystalline cellulose | 39.25 to 41.8 |
| Lactose Fast Flo ® | 45.00 |
| Polyvinylpyrrolidone (Plasdone K29/32) | 10.00 |
| Crosslinked Polyvinylpyrrolidone (Plasdone XL 10) | 3.00 |
| Magnesium Stearate | 1.00 |
| Total | 100.00 |

TABLE 7-continued

| | Milligram/tablet |
|---|---|
| Second Layer Ingredients | |
| Pseudoephedrine HCl | 120.00 |
| Microcrystalline cellulose | 39.00 |
| Hydroxypropylmethyl cellulose | 45.00 |
| Polyvinylpyrrolidone (Plasdone K29/32) | 5.00 |
| Magnesium Stearate | 1.00 |
| Total | 210.00 |

The first layer is formed by charging brompheniramine maleate, cetirizine HCl, microcrystalline cellulose, and Lactose Fastflo into a blender and mixed. Plasdone K29/32 and Plasdone XL10 are passed through a # 30 mesh screen, added to the blender and mixed. Magnesium stearate is passed through a # 30 mesh screen and added to the blender and mixed to form a final first layer blend.

Charge Pseudoephedrine HCl, microcrystalline cellulose, and Hydroxypropyl methyl cellulose into a granulator. Granulate the powder mix with Plasdone K29/32 solution. Dry the granules. Mill the dried granules and blend with Magnesium stearate that was screened through a # 30 mesh screen to form a final second extended release layer blend. Bilayer tablets are formed by compressing 100 mg of the final first layer blend and 210 mg of the final second layer blend.

Example 8

Tablets (Extended Release)

A coated tablet is formed having 2.5 to 10.0 diphenhydramine HCl as the first antihistamine and 9.0 to 10.0 mg loratadine as the second antihistamine, where both antihistamines are formulated as an immediate release coating layer on a 120 to 240 mg Pseudoephedrine sulfate (additional active agent) extended-release tablet core.

Example 9

Tablets (Extended Release)

A coated tablet is formed having 2.5 to 10.0 diphenhydramine HCl as the first antihistamine and 9.0 to 10.0 mg loratadine as the second antihistamine, where both antihistamines are formulated as an immediate release coating layer on a leukotriene receptor antagonist-containing extended-release tablet core. The tablet core can contain 5.2 to 10.4 montelukast sodium or 10 to 40 mg zafirlukast as the leukotriene receptor antagonist as the additional active agent. Within this embodiment, the loratadine can be replaced with 60.0 to 180.0 mg fexofenadine HCl or 9.0 to 10 mg cetirizine HCl.

The terms "comprising", "having", "including", and "containing" are to be construed as open-ended terms (i.e., meaning "including, but not limited to"). The terms "a" and "an" do not denote a limitation of quantity, but rather denote the presence of at least one of the referenced item. The term "or" means "and/or". The endpoints of all ranges directed to the same component or property are inclusive and independently combinable. The modifier "about" used in connection with a quantity is inclusive of the stated value and has the meaning dictated by the context (e.g., includes the degree of error associated with measurement of the particular quantity). The term "or a combination thereof" means a combination of one, two, or more of the listed items.

Unless defined otherwise, technical and scientific terms used herein have the same meaning as is commonly understood by one of skill in the art to which this invention belongs.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of orally administering an antihistamine combination, comprising:
   concomitantly orally administering to a human patient in need thereof
   a first generation antihistamine in an attenuated dosage amount to provide a quick onset of action wherein the patient experiences substantially no sedative effect;
   a second or third generation antihistamine in a maintenance dosage amount to provide continued antihistaminic effect; and
   an additional active agent, where the additional active agent is a decongestant, a cough suppressant (an antitussive), a leukotriene receptor antagonist, a 5-lipoxygenase inhibitor, a bronchodilator, an expectorant, or a combination thereof,
   wherein the administering can occur regardless of the time of day.

2. The method of claim 1, wherein the first generation antihistamine, the second or third generation antihistamine, and the additional active agent are formulated
   as a single oral dosage form;
   each formulated as an individual oral dosage form; or
   two of the first generation antihistamine, the second or third generation antihistamine, and the additional active agent are formulated as a single oral dosage form and the third is formulated as an individual dosage form.

3. The method of claim 2, wherein each oral dosage form is individually a tablet, a capsule, a pellet, a film, a solution, a suspension, an emulsion, a powder, or a granule.

4. The method of claim 1, wherein
   the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof;
   the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof;
   the decongestant is pseudoephedrine, phenylephrine, a pharmaceutically acceptable salt thereof, or a combination thereof;
   the cough suppressant is dextromethorphan, benzonatate, an opioid, a pharmaceutically acceptable salt thereof, or a combination thereof;
   the leukotriene receptor antagonist is montelukast, zafirlukast, pranlukast, a pharmaceutically acceptable salt thereof, or a combination thereof,
   the 5-lipoxygenase inhibitor is zileuton, meclofenamic acid, *Hypericum perforatum* (St. John's wort), a pharmaceutically acceptable salt thereof, or a combination thereof; and
   the bronchodilator is leukotriene receptor antagonists, beta-adrenergic agonists, anticholinergic, corticosteroids, mast cell stabilizers, a pharmaceutically acceptable salt thereof, or a combination thereof.

5. The method of claim 1, wherein
   the first generation antihistamine is
   brompheniramine maleate in an attenuated dosage amount of about 0.4 mg to about 3.6 mg, about 0.5 mg to about 3.0 mg, about 0.75 mg to about 2.5 mg, or about 1.0 mg to about 2.0 mg;
   chlorpheneramine maleate in an attenuated dosage amount of about 0.2 mg to about 1.75 mg, about 0.5 mg to about 1.5 mg, or about 0.75 mg to about 1.0 mg;
   clemastine fumarate in an attenuated dosage amount of about 0.268 mg to about 2.4 mg, or about 0.3 mg to about 2.0 mg, or about 0.7 mg to about 1.5 mg;
   cyproheptadine hydrochloride in an attenuated dosage amount of about 0.4 mg to about 3.6 mg, about 0.6 mg to about 3.0 mg, or about 1.0 mg to about 2.0 mg;
   diphenhydramine hydrochloride in an attenuated dosage amount of about 2.5 mg to about 23 mg, about 3.5 mg to about 15 mg, about 4.0 mg to about 10 mg, or about 5.0 mg to about 6.25 mg;
   doxylamine succinate in an attenuated dosage amount of about 0.625 mg to about 6.0 mg, about 1.0 mg to about 4.0 mg, about 1.5 mg to about 3.0 mg, or about 2.0 mg to about 2.5 mg;
   pheniramine maleate in an attenuated dosage amount of about 2.5 mg to about 23 mg, about 5.0 mg to about 20.0 mg, or about 10.0 mg to about 15.0 mg;
   promethazine hydrochloride in an attenuated dosage amount of about 1.25 mg to about 8.125 mg, about 2.0 mg to about 6.0 mg, or about 3.0 mg to about 5.0 mg;
   triprolidine hydrochloride in an attenuated dosage amount of about 0.25 mg to about 1.625 mg, about 0.5 mg to about 1.5 mg, or about 0.75 mg to about 1.0 mg; or a combination thereof; and
   the second or third generation antihistamine is
   acrivastine in an amount of about 7.2 mg to about 8.0 mg;
   cetirizine hydrochloride in an amount of about 9.0 mg to about 10 mg;
   desloratadine in an amount of about 2.25 to about 5 mg, about 2.25 to about 2.5 mg, or about 4.5 mg to about 5 mg;
   fexofenadine hydrochloride in an amount of about 54 mg to about 180 mg, about 54 mg to about 60 mg, or about 108 mg to about 120 mg, or about 162 mg to about 180 mg;
   levocetirizine dihydrochloride in an amount of about 4.5 mg to about 5 mg,
   loratadine in an amount of about 9.0 mg to about 10 mg,
   terfenadine in an amount of about 54 mg to about 60 mg, or a combination thereof.

6. The method of claim 1, to be administered once a day or twice a day.

7. The method of claim 1, wherein the first generation antihistamine when administered to a patient provides therapeutic prophylactic and symptomatic treatment of seasonal or perennial allergic rhinitis, vasomotor rhinitis, or other respiratory allergies for the first 1 hour after administration or for the first 2 hours after administration.

8. The method of claim 1 for pediatric use.

9. The method of claim 1, wherein
the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof;
the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; and
the decongestant is pseudoephedrine, phenylephrine, a pharmaceutically acceptable salt thereof, or a combination thereof.

10. The method of claim 1, wherein
the first generation antihistamine is brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, a pharmaceutically acceptable salt thereof, or a combination thereof;
the second or third generation antihistamine is acrivastine, astemizole, cetirizine, desloratadine, fexofenadine, levocetirizine, loratadine, mizolastine, terfenadine, a pharmaceutically acceptable salt thereof, or a combination thereof; and the leukotriene receptor antagonist is montelukast, zafirlukast, pranlukast, a pharmaceutically acceptable salt thereof, or a combination thereof;
the leukotriene receptor antagonist is montelukast, zafirlukast, pranlukast, a pharmaceutically acceptable salt thereof, or a combination thereof.

11. The method of claim 1, wherein
a first generation antihistamine in an attenuated dosage amount to provide a quick onset of action wherein the patient experiences substantially no sedative effect;
a second or third generation antihistamine in a maintenance dosage amount to provide continued antihistaminic effect; and
an additional active agent, where the additional active agent is a decongestant, a cough suppressant (an antitussive), a leukotriene receptor antagonist, a 5-lipoxygenase inhibitor, a bronchodilator, an expectorant, or a combination thereof.

* * * * *